(12) United States Patent
Hawley

(10) Patent No.: US 7,547,522 B2
(45) Date of Patent: Jun. 16, 2009

(54) METHOD TO ENRICH FOR α(1,3)-GALACTOSYLTRANSFERASE NULL PIG CELLS

(75) Inventor: Robert J. Hawley, Wayland, MA (US)

(73) Assignee: Immerge Biotherapeutics, Inc., Cambridge, MA (US)

( * ) Notice: Subject to any disclaimer, the term of this patent is extended or adjusted under 35 U.S.C. 154(b) by 181 days.

(21) Appl. No.: 10/524,381

(22) PCT Filed: Aug. 13, 2003

(86) PCT No.: PCT/US03/25199
§ 371 (c)(1),
(2), (4) Date: Oct. 3, 2005

(87) PCT Pub. No.: WO2004/016742
PCT Pub. Date: Feb. 26, 2004

(65) Prior Publication Data
US 2006/0242722 A1 Oct. 26, 2006

Related U.S. Application Data

(60) Provisional application No. 60/403,405, filed on Aug. 14, 2002.

(51) Int. Cl.
*G01N 33/53* (2006.01)
*G01N 33/567* (2006.01)
(52) U.S. Cl. .................. 435/7.21; 435/7.2; 435/7.1
(58) Field of Classification Search .................. None
See application file for complete search history.

(56) References Cited

U.S. PATENT DOCUMENTS

| 5,821,117 | A |   | 10/1998 | Sandrin et al. |
| 5,849,991 | A |   | 12/1998 | D'Aspice et al. |
| 6,153,428 | A | * | 11/2000 | Gustafsson et al. ......... 435/325 |
| 6,166,288 | A |   | 12/2000 | Diamond et al. |
| 6,331,658 | B1 |  | 12/2001 | Cooper et al. |
| 6,413,769 | B1 |  | 7/2002 | Gustafsson et al. |

FOREIGN PATENT DOCUMENTS

| WO | WO-95/20661 | 8/1995 |
| WO | WO 95/28412 A1 | 10/1995 |
| WO | WO 97/16064 | 5/1997 |
| WO | WO 01/88096 | 11/2001 |

OTHER PUBLICATIONS

Evans, R.W., "Coming to Terms with Reality: Why Xenotransplantation is a necessity", Xenotransplantation, J.L. Platt, Ed., ASM Press, Wash., DC, 29-51 (2001).
Lambrigts et al., "Discordant Organ Xenotransplantation in Primates", Transplantation, 66(5):547-561 (1998).
Costa et al., "Expression of the Human 1,2-Fucosyltransferase in Transgenic pigs Modifies the Cell Surface Carbohydrate Phenotype and Confers Resistance to Human Serum-Mediated Cytolysis", FASEB J., 13:1762-1773 (1999).
Miyagawa et al., "Remodeling of the Major Pig Xenoantigen by N-Acetylglucosaminyltransferase III in Transgenic Pig", J. Biol. Chem., 276(42):39310 39319 (2001).
Thall et al., "Oocyte Galα1,3Gal Epitopes Implicated in Sperm Adhesion to the Zona Pellucida Glycoprotein ZP3 are Not Required for Fertilization in the Mouse", J. Biol. Chem., 270(37):21437-21440 (1995).
Park et al., Anim. Biotech., In Press (2001).
Dai et al., "Targeted Disruption of the α1,3-Galactosyltransferase Gene in Cloned Pigs" Nature Biotechnol., 20(3):251-255 (2002).
Lai et al., "Production of α-1,3-Galactosyltransferase Knockout Pigs by Nuclear Transfer Cloning" Science, 295:1089-1092 (2002).
Bondioli et al., "Cloned Pigs Generated From Cultured Skin Fibroblasts Derived From a H-Transferase Transgenic Boar", Mol. Reproduc. Dev., 60:189-195 (2001).
Sachs et al., "Transplantation in Miniature Swine", Transplantation, 22(6):559-567 (1976).
Nozawa, S. et al., "Characteristics of Immunoglobulin Gene Usage of the Xenoantibody Binding to . . . " Transplantation, 72(1):147-155 (2001).
Ayares, D. et al., "Cloning Pigs Deficient in Alpha 1,3 Galactosyltransferase" Graft, 4(1):80-82 (2001).
Gock, H. et al., "Deleting the Gal Epitope from the Donor Pig" Graft, 4(1):76-77 (2001).
Miyagawa, S. et al., "Masking and Reduction of the Galactose-Alpha 1,3-Galactose (alpha-Gal) Epitope, the Major Xenoantigen in Swine, by the Glycosyltransferase Gene Transfection", Biochemical and Biophysical Research Communications, 264:611-614 (1999).
Sao, H. et al., "A New Marrow T Cell Depeletion Method Using Anti-CD6-Monoclonal Antibody-Conjugated Magnetic Beads and its Clinical Application for Prevention of Actue Graft-vs.-Host Disease in Allogeneic Bone Marrow Transplantation: Results of a Phase I-II Trial", International Journal of Hematology, 69:27-35 (1999).
Polejaeva, I.A. et al., "Cloned Pigs Produced by Nuclear Transfer from Adult Somatic Cells", Nature, 407:86-90 (2000).
Onishi, A. et al., "Pig Cloning by Mocroinjection of Fetal fibroblast Neclei", Science, 289:1188-1190 (2000).
Betthauser, J. et al., "Production of Cloned Pigs from In Vitro Systems", Nature Biotechnology, 18:1055-1059 (2000).

(Continued)

*Primary Examiner*—Deborah Crouch
(74) *Attorney, Agent, or Firm*—Margo H. Furman; Choate Hall & Stewart, LLP

(57) ABSTRACT

The invention relates to the genetic manipulation of non-human animals. More particularly, the invention relates to genetic manipulation of non-human animals to be used for xenotransplantation. The invention provides a method of selecting GGTA 1 null cells, a viable GGTA 1 null swine, methods for making such swine, and methods of using cells, tissues and organs of such swine for xenotransplantation.

15 Claims, 13 Drawing Sheets

OTHER PUBLICATIONS

McCreath, K.J. et al., "Production of Gene-Targeted Sheep by Nuclear Transfer From Somatic Cells", *Nature*, 405:1066-1069 (2000).

McKenzie et al., "Strategies to overcome hyperacute rejection of pig-to-human xenografts," Transplantation Proceedings, vol. 29, No. 1/2, pp. 973-974 (1996).

R.G. Tearle et al., "The [alpha]-1,3-Galactosyltransferase Knockout Mouse: Implications for Xenotransplantation [Rapid Communication]", *Transplantation (Baltimore)*, vol. 61, No. 1, pp. 1-9 (1996).

A.D. Thall, "Generation of α 1,3Galactosyltransferase Deficient Mice", *Sub-Cellular Biochemistry*, vol. 32, pp. 259-279 (1999).

A. Sepp et al., "Inhibition of Expression of the Galα1-3Gal Epitope on Porcine Cells Using an Intracellular Single-Chain Antibody Directed Against α1,3Galactosyltransferase", *Journal of Immunological Methods* (Elsevier Science Publishers B.V., Amsterdam, NL), vol. 231, No. 1-2, pp. 191-205 (Dec. 10, 1999).

C.J. Phelps et al., "Production of α1,3-Galactosyltransferase Deficient Pigs", *Science*, American Association for the Advancement of Science, vol. 299, pp. 411-414 (Jan. 17, 2003).

* cited by examiner

Figure 3A.
Figure 3B.
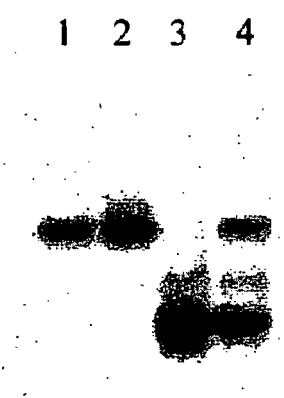
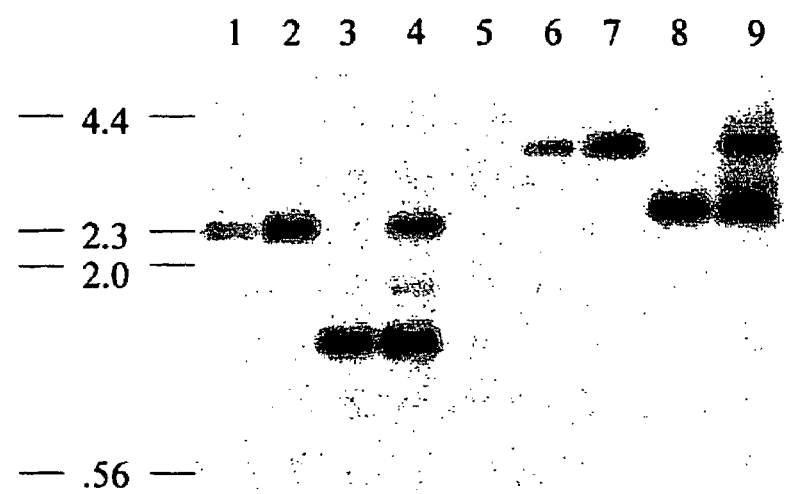

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ttctgcagag cagagctcac                                              20

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccctcaaccc agaacagata ag                                           22

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 3
aggatgtgcc ttgtaccacc                                                    20

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gaagaagacg ctataggcaa cg                                                 22
```

METHOD TO ENRICH FOR α(1,3)-GALACTOSYLTRANSFERASE NULL PIG CELLS

RELATED APPLICATIONS/PATENTS

This application is the U.S. national phase application, pursuant to 35 U.S.C. § 371, of International Patent Application No. PCT/US2003/025199, having an international filing date of Aug. 13, 2003, designating the United States, and published in English on Feb. 26, 2004 as International Publication No. WO 2004/016742 A2, which claims priority to U.S. Application Ser. No. 60/403,405 filed on Aug. 14, 2002.

This invention has been funded in part by the National Institutes of Health NCRR via R44 RR15198. The U.S. government has rights in this invention.

BACKGROUND OF THE INVENTION

1. Field of the Invention

The invention relates to the genetic manipulation of non-human animals. More particularly, in some embodiments, the invention relates to selecting α(1,3)-galactosyltransferase (GGTA1) null cells and genetic manipulation of non-human animals to be used for xenotransplantation.

2. Summary of the Related Art

Clinical transplantation has become one of the major treatments for end stage organ failure since the introduction of chronic immunosuppressive drugs in the mid 1980s. This success has brought about the secondary issue of human organ supply, which greatly limits the ability to provide organs to patients in need of transplants. One of the major approaches to solving this medical need is the utilization of alternative species as a source of organs (xenotransplantation). R. W Evans, in *Xenotransplantation*, J. L. Platt, Ed. (ASM Press, Washington, D.C., 2001), pp. 29-51, teaches that the pig is the primary alternative species due to ethical considerations, breeding characteristics, infectious disease concerns and its compatible size and physiology.

A major barrier to progress in pig-to-primate organ transplantation is the presence of terminal α(1,3)-galactosyl-(gal)-epitopes on the surface of pig cells. Humans and Old World monkeys have lost the corresponding galactosyltransferase activity in the course of evolution and therefore produce preformed natural antibodies against the epitopes that are responsible for hyperacute rejection of porcine organs. The temporary removal of recipient anti-gal antibodies through affinity adsorption and expression of complement regulators in transgenic pigs has allowed survival of pig organs beyond the hyperacute rejection stage. However, D. Lambrigts, D. H. Sachs, D. K. S Cooper, *Transplantation* 66, 547 (1998), teaches that returning antibody and residual complement activity are likely to be responsible for the acute and delayed damage which severely limits organ survival even in the presence of high levels of immunosuppressive drugs and other clinical intervention. Attempts have also been made to prevent rejection by reducing expression of gal epitopes through genetic engineering of the donor animal. Unfortunately, C. Costa et al., *FASEB J.* 13, 1762 (1999), discloses that competitive inhibition of galtransferase in H-transferase transgenic pigs results in only partial reduction in epitope numbers. Other similar approaches have been disclosed in Sandrin et al U.S. Pat. No. 5,821,117, Diamond et al U.S. Pat. No. 6,166,288, and Cooper et al U.S. Pat. No. 6,331,658, all teaching methods for masking the gal epitope through the genetically modified increased expression of carbohydrate epitopes. Similarly, S. Miyagawa et al., *J. Biol. Chem.* 276, 39310 (2001), teaches that attempts to block expression of gal epitopes in N-acetylglucosaminyltransferase III transgenic pigs also results in only partial reduction of gal epitopes numbers and fails to significantly extend graft survival in primate recipients. Given the large number of gal epitopes present on pig cells, it seems unlikely that any dominant transgenic approach of this nature can provide sufficient protection from anti-gal mediated damage.

A. D. Thall, P. Maly, J. B. Lowe, *J. Biol. Chem.* 270, 21,437 (1995), and D'Aspice et al, U.S. Pat. No. 5,849,991 teach that viable GGTA1 knockout mice can be produced using ES cell technology. K. L. McCreath et al., *Nature* 405, 1066 (2000), and Denning et al. PCT Publication WO 01/88096 teach that nuclear transfer technology can be used for locus specific modification of certain large animals, as demonstrated by the production of viable sheep using in vitro targeted somatic cells. K. W. Park et al., *Anim. Biotech*. In press (2001), discloses successful cloning and production of transgenic pigs by nuclear transfer of genetically modified somatic cells. Gustafsson and Sachs, U.S. Pat. No. 6,153,428 (2000), discloses genetically modified porcine cells in vitro in which the GGTA1 gene has been disrupted by homologous recombination. Dai et al, *Nature Biotechnol.* 20 (3): 251-255 (2002) teaches production of a pig heterozygous for GGTA1 disrupted gene and Lai et al, *Science*. 295: 1089 (2002) teaches production of a miniature swine heterozygous for GGTA1 disrupted gene. Gustaffson et al. U.S. Pat. No. 6,413,769 teaches the use of a synthetic antisense oligonucleotide (S-oligonucleotides) to create inactivated heterozygous GGTA1 disrupted miniature porcine cells. Gustaffson et al. further teaches the generation of heterozygous miniature swine by using a drug selection system whereby a vector delivers an antibacterial resistant sequence i.e. neomycin resistant, into the genome to render the GGTA1 gene inactivated. Unfortunately, Bondioli et al., *Mol. Reproduc. Dev.* 60: 189-195 (2001) reports that the attempt to use nuclear transfer technology to accomplish this in pigs in vivo has been unsuccessful. This is further reported by Ioannu et al, PCT publication WO 97/16064 which discloses that a knockout pig cannot be done.

Gustaffson further discloses in U.S. Pat. No. 6,413,769 the possibility of using antisense technology to produce a miniature swine functionally unable to produce α(1,3)-galactosyltransferase and a method for generation of homozygous miniature swine using a second drug selection system such as herpes simplex virus-thymidine kinase (HSV-tk). Unfortunately, he does not demonstrate that a viable homozygous swine was produced using either method and does not demonstrate that cells were able to be produced and validated for GGTA1 disrupted gene.

There is, therefore, a need for viable GGTA1 null swine defined as swine which do not express any GGTA1 epitopes and which include but are not limited to swine having both alleles of the GGTA1 gene disrupted or rendered non-functional; and swine having one copy of the GGTA1 allele instead of the usual two alleles for the GGTA1 gene and the said copy of the GGTA1 allele is disrupted or rendered non-functional. There is also a need for methods for making such GGTA1 null swine; and methods of using the tissues and organs of such GGTA1 null swine for xenotransplantation.

BRIEF SUMMARY OF THE INVENTION

The invention provides viable GGTA1 null swine, methods to produce such swine, including the breeding of two GGTA1 null swine to produce GGTA1 null swine progeny, and methods of using cells, tissues and organs of such swine for xenotransplantation.

In a first aspect, the invention provides viable GGTA1 null swine. Such swine are useful as a source of organs, tissues, and cells for xenotransplantation. Such swine are also useful for providing a clearer evaluation of approaches currently in development aimed at overcoming potential delayed and chronic rejection mechanisms in porcine xenotransplantation.

In a second aspect, the invention provides a method of selecting GGTA1 null cells comprising obtaining a line of cells from a heterozygous GGTA1 swine or swine fetus in which one allele of the GGTA1 gene has been disrupted or rendered non-functional; enriching the cell line for GGTA1 null cells, and scanning said cell line for viable GGTA1 null cells.

In a third aspect, the step of enriching the cell line for GGTA1 null cells is accomplished by at least one treatment selected from the group consisting of: treating said line with anti-galactose-α(1,3)-galactose antibodies in the presence of complement; depleting the line using magnetic beads which are preferably bound with an anti-gal reagent such as an antibody or lectin; treating said line with anti-galactose-α(1,3)-galactose antibodies and then depleting the line using magnetic beads bound to an anti-antibody; and treating said line with gal epitope ligands and then depleting said line with magnetic beads coated with anti ligand antibodies. Such GGTA1 null cell enriching treatment can comprise multiple treatments selected from the group above.

In a fourth aspect, the invention provides a GGTA1 null porcine cell. Such cells lack the galactose-α(1,3)-galactose epitopes and are useful in overcoming hyperacute rejection in primates.

In a fifth aspect, the invention provides porcine organs lacking expression of galactose-α(1,3)-galactose epitopes and comprising GGTA1 null cells. Such organs are useful in overcoming hyperacute rejection in primates.

In a sixth aspect, the invention provides porcine tissues lacking expression of galactose-α(1,3)-galactose epitopes and comprising GGTA1 null cells. Such tissues are useful in overcoming hyperacute rejection in primates.

In a seventh aspect, the invention provides a method of creating a viable GGTA1 null swine comprising isolating GGTA1 null cells, enucleating an oocyte, fusing the oocyte with the disrupted cell to yield an NT-derived embryo, and implanting the NT-derived embryo into a surrogate mother, wherein the surrogate mother has initiated estrus, but has not yet completed ovulation.

In an eighth aspect, the invention provides a method of creating a viable GGTA1 null swine comprising enucleating an oocyte, fusing the oocyte with a cell derived from Q2 to yield an NT-derived embryo, and implanting the NT-derived embryo into a surrogate mother, wherein the surrogate mother has initiated estrus, but has not yet completed ovulation.

In a ninth aspect, the invention provides a method of creating a viable GGAT1 null swine comprising enucleating an oocyte, fusing the oocyte with a cell derived from Q9 to yield an NT-derived embryo, and implanting the NT-derived embryo into a surrogate mother, wherein the surrogate mother has initiated estrus, but has not yet completed ovulation.

In a tenth aspect, the invention provides a method of creating a viable GGTA1 null swine comprising enucleating an oocyte, fusing the oocyte with a cell derived from Q32 to yield an NT-derived embryo, and implanting the NT-derived embryo into a surrogate mother, wherein the surrogate mother has initiated estrus, but has not yet completed ovulation.

In an eleventh aspect, the invention provides a method of creating a viable GGTA1 null swine comprising enucleating an oocyte, fusing the oocyte with a cell derived from Q37 to yield an NT-derived embryo, and implanting the NT-derived embryo into a surrogate mother, wherein the surrogate mother has initiated estrus, but has not yet completed ovulation.

BRIEF DESCRIPTION OF THE DRAWINGS

FIG. 3A. RT-PCR analysis of clones Q2 and Q9, derived by antibody/complement selection of GGTA1 heterozygous cells from fetus 355-F1. Lane 1: Q2. Lane 2: Q9. Lane 3: F12 (WT fetal fibroblast control). Lane 4: 355-F1 cells prior to antibody/complement selection. Lambda Hind III marker sizes are indicated in kbp. 2472 bp targeted locus and 1421 bp wild-type locus PCR products are detected in 355-F1 cells prior to selection, but only the 2472 bp product is detected in clones Q2 and Q9.

FIG. 3B. Genomic analysis of clones Q2 and Q9, derived by antibody/complement selection of GGTA1 heterozygous cells from fetus 355-F1. Lanes 1-4: 3' targeting analysis. Lane 1: Q2. Lane 2: Q9. Lane 3: F505 (WT fetal fibroblast control). Lane 4: 355-F1 cells prior to antibody/complement selection. Lambda Hind III marker sizes are indicated in kbp. 2.3 kbp targeted locus and 1.25 kbp wild-type locus PCR products are detected in 355-F1 cells prior to selection, but only the 2472 bp product is detected in clones Q2 and Q9. Lanes 6-9: 5' targeting analysis. Lane 6: Q2. Lane 7: Q9. Lane 8: F505 (WT fetal fibroblast control). Lane 9: 355-F1 cells prior to antibody/complement selection. 3.6 kbp targeted locus and 2.55 kbp wild-type locus PCR products are detected in 355-F1 cells prior to selection, but only the 2472 bp product is detected in clones Q2 and Q9.

DETAILED DESCRIPTION OF THE PREFERRED EMBODIMENTS

Figure 1:
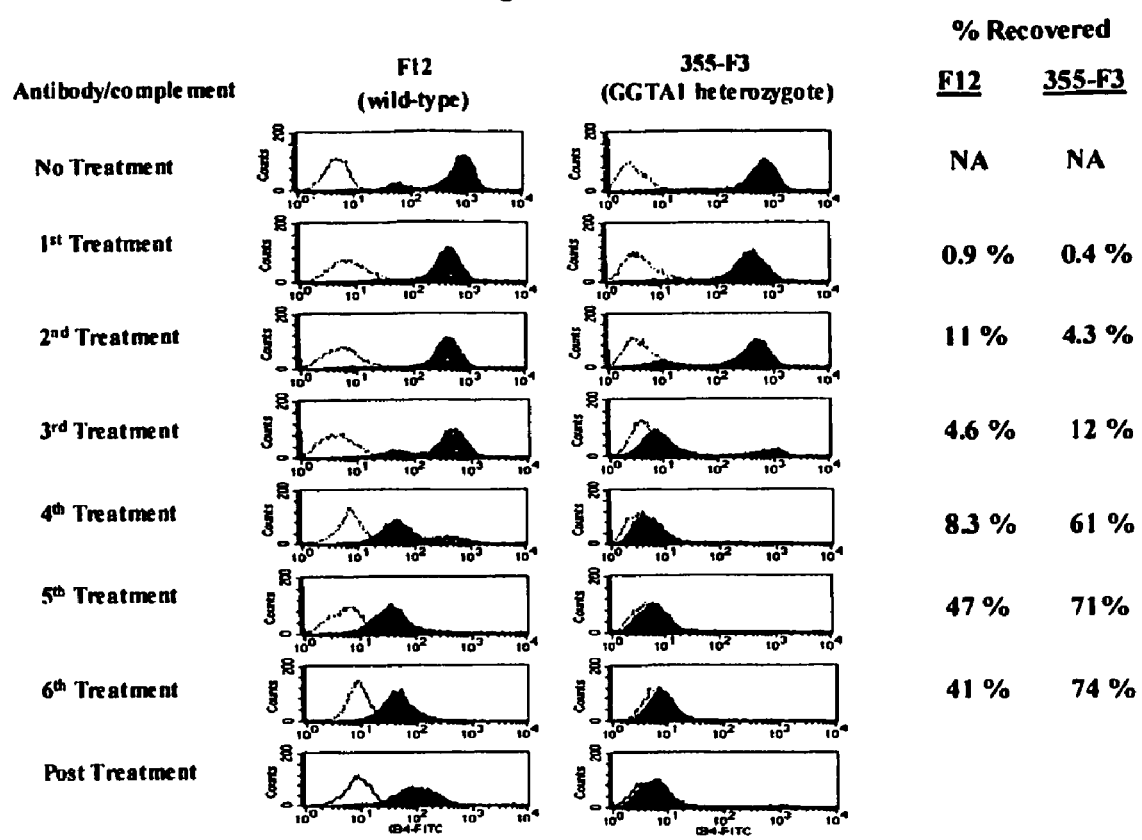
FIG. 1. Flow cytometric analysis of wild-type (F12) and GGTA1 heterozygous (355-F3) fetal cells following multiple rounds of selection with antibody and complement. Cells were analyzed prior to (open traces) or following (filled traces) staining with α(1,3)-gal epitope specific lectin IB4. Cells were analyzed 5-9 days following each selection. Post treatment analyses were performed 17 days following the last selection for F12 cells, and 22 days following the last selection for 355-F1 cells. The percentage of cells recovered immediately following antibody/complement selection is indicated, and includes all cell losses during the treatment procedure.

The invention relates to the genetic manipulation of non-human animals. More particularly, the invention relates to genetic manipulation of non-human animals to be used for xenotransplantation. The invention provides viable GGTA1 null swine, methods for making such swine, including the breeding of two GGTA1 null swine to produce GGTA1 null swine progeny, and methods of using cells, tissues and organs of such swine for xenotransplantation.

The patents and publications cited herein reflect the knowledge in the art and are hereby incorporated by reference in their entirety. Any inconsistency between these patents and publications and this specification shall be resolved in favor of the latter.

In a first aspect, the invention provides a viable GGTA1 null swine. For the purposes of the invention "GGTA1 null swine" are swine which do not express any GGTA1 epitopes and which include but are not limited to swine having both alleles of the GGTA1 gene disrupted or rendered non-functional; and swine having one copy of the GGTA1 allele instead of the usual two alleles for the GGTA1 gene and the said allele is disrupted or rendered non-functional. By "disrupted gene" is meant a portion of the genetic code that has been altered, thereby affecting transcription and/or translation of that segment of the genetic code, e.g., rendering that segment of the code unreadable through knockout techniques or by insertion of an additional gene for a desired protein or insertion of a regulatory sequence that modulates transcription of an existing sequence. In certain embodiments, the GGTA1 allele is altered by homologous recombination or other insertion or deletion. In certain embodiments, the GGTA1 allele is non-functional due to mutation.

In certain embodiments, the GGTA1 null swine is a swine in which, both alleles of the GGTA1 gene are disrupted or rendered non-functional, herein referred to as "homozygous". Such embodiments include those commonly referred to as "gene knockouts", "gene knock-ins" and any other modification of both native alleles of the native GGTA1 gene that renders such gene non-functional.

In certain embodiments, the GGTA1 null swine is a swine which only has one allele of the GGTA1 gene instead of possessing the usual two GGTA1 alleles, herein referred to as "hemizygous" and the single allele of the GGTA1 gene is disrupted or rendered non-functional.

In certain embodiments, the GGTA1 null swine is a "compound heterozygote" for the GGTA1 gene, in which the swine possesses two different mutant alleles for the GGTA1 gene, so that the GGTA1 gene is rendered non-functional.

In certain preferred embodiments, the GGTA1 null swine is a miniature swine. In certain preferred embodiments, the GGTA1 null swine is a miniature swine which is a descendant from the miniature swine disclosed in Sachs et al., *Transplantation* 22, 559 (1976).

Such GGTA1 null swine are useful as a source of organs, tissues and cells for xenotransplantation. Such swine are also useful for providing a clearer evaluation of approaches currently in development aimed at overcoming potential delayed and chronic rejection mechanisms in porcine xenotransplantation.

In a second aspect, the invention provides a method of selecting GGTA1 null cells comprising obtaining a line of cells from a heterozygous GGTA1 swine or swine fetus in which one allele of the GGTA1 gene has been disrupted or rendered non-functional; enriching the cell line for GGTA1 nulls cells, and scanning said cell line for viable GGTA1 null cells. For the purposes of the invention, "scanning" means any method used to validate the presence of the disrupted gene. Methods of such scanning are well known to those skilled in the art and include but are not limited to staining with lectins, flow cytometry, PCR, RT-PCR and Southern Blots. For the purposes of the invention a "line" is a group of cells derived from the same source. Methods of obtaining such lines are well known to those skilled in the art. One non-limiting example of obtaining a line includes isolation of primary fibroblasts from miniature swine fetus by collegenase/trypsin digestion of minced tissue, plating the dissociated cells on collagen-coated plates in nutrient medium containing one or more reagents such as Hams FIO medium, Duelbecco's Modified Eagle's Medium (DMEM), Fetal Bovine Serum (FBS), and antibiotics such as gentamycin, adherent cells are then cryopreserved and function as the "line". In certain preferred embodiments, the heterozygous GGTA1 swine is a miniature swine and is produced according to the methods disclosed in Lai et al, *Science* 295:1089 (2002). In certain preferred embodiments, the heterozygous GGTA1 swine is a miniature swine, which is a descendant of the miniature swine disclosed in Sachs et al, *Transplantation* 22, 559 (1976). In certain preferred embodiments, the swine fetus with one disrupted GGTA1 allele is obtained from a descendant of the miniature swine disclosed in Sachs et al, *Transplantation* 22, 559 (1976).

In certain preferred embodiments, the line of cells is obtained by isolating GGTA1 heterozygous cells from a nuclear transfer fetus after gestation and culturing the said cells as described in Lai et al., *Science* 295:1089 (2002). In certain preferred embodiments, the line of cells is a clonal population of porcine fetal fibroblast cells. For the purposes of the invention a "clonal population" is a group of cells derived from a single cell. Porcine fetal fibroblast cells of the invention may be obtained through techniques known to those skilled in the art and include but are not limited to mincing porcine fetal tissue and digestion of tissue with collagenase and trypsin. In certain preferred embodiments the porcine fetal fibroblasts cells are obtained from miniature swine descendant from the miniature swine disclosed in Sachs el al., *Transplantation* 22, 559 (1976). In certain preferred embodiments the porcine fetal fibroblasts cells are heterozygous for a GGTA1 knockout. In preferred embodiments the cells heterozygous for a GGTA1 knockout are obtained from descendants from the miniature swine disclosed in Lai et al., *Science* 295:1089 (2002).)

In a third aspect, the step of enriching the cell line for GGTA1 null cells described in the second aspect is accomplished by at least one treatment selected from the group consisting of: treating said line with anti-galactose-α(1,3)-galactose antibodies in the presence of complement; depleting the line using magnetic beads which are preferably bound with an anti-gal reagent; treating said line with anti-galactose-α(1,3)-galactose antibodies and then depleting the line using magnetic beads bound to an anti-antibody; and treating said line with gal epitope ligands and then depleting said line with magnetic beads coated with anti ligand antibodies. In certain preferred embodiments, such GGTA1 null cell enriching treatment comprises multiple treatments selected from the group above. In certain preferred embodiments, such GGTA1 null cell enriching treatment comprises a combination of multiple treatments selected from the group above. For the purposes of the invention, an "anti-gal reagent" is a reagent which binds to galactose-α(1,3)-galactose and includes but not limited to anti-galactose-α(1,3)-galactose antibody and lectin.

In certain preferred embodiments the anti-galactose-α1,3-galactose antibodies are primate antibodies. Antibodies of the invention can be derived from but are not limited to baboon, chimpanzee, gorilla, human and other primates with the ability to produce antibodies to the α(1,3)-galactosyl-(gal)-epitopes. For the purposes of the invention a "primate" is given its dictionary meaning as defined in Merriam-Webster (2002) and "includes any of an order (Primates) of mammals comprising humans, apes, monkeys, and related forms (as lemurs and tarsiers). Antibodies of the invention include but are not limited to monoclonal antibodies and fragments thereof. In preferred embodiments, the primate antibody is derived from baboon plasma.

In certain preferred embodiments, the gal epitope ligands include but are not limited to IB4 conjugates, such as IB4 Biotin (SIGMA, L2140) and IB4-FITC and the anti-ligand antibodies include but are not limited to anti-biotin and anti-FITC.

In certain preferred embodiments, the step of enriching the cell line for GGTA1 null cells comprises multiple treatments of anti-galactose-α(1,3)-galactose antibodies in the presence of complement, followed by multiple treatments of depletion using IB4-FITC and magnetic micro-beads coated with anti-FITC.

All other parameters are as described for the third aspect.

In a fourth aspect, the invention provides GGTA1 null porcine cells that are useful for xenotransplantation. For the purposes of the invention, "GGTA1 null cells" are cells lacking the α(1,3)-galactosyl-(gal)-epitopes and include but are not limited to cells which are be homozygous, which comprise two disrupted or non-functional GGTA1 genes; hemizygous, which comprise one GGTA1 alleles instead of the usual two alleles for the GGTA1 gene and that the single GGTA1 allele is disrupted or rendered non-functional; or compound heterozygous, which comprise two different mutant alleles for the GGTA1 gene. Such cells are derived from a swine according to the first aspect of the invention. Preferred cells include, without limitation, Islets of Langerhans cells, blood precursor cells, bone precursor cells, and stem cells, including primordial stem cells. More preferably the cell is Q2, Q9, Q32 or Q37 derived therefrom. Such GGTA1 null cells are useful in overcoming hyperacute rejection in primates.

In a fifth aspect, the invention provides porcine organs that are useful for xenotransplantation. Such porcine organs comprise GGTA1 null cells and lack the α(1,3) galactosyl (gal) epitopes that are responsible for hyperacute rejection in primates. Such organs are derived from a swine according to the first aspect of the invention. For purposes of the invention, an "organ" is an organized structure comprising one or more tissues, which organ performs one or more specific biological function. Preferred organs include, without limitation, heart, liver, kidney, pancreas, lung, thyroid, and skin.

In a sixth aspect, the invention provides tissues that are useful for xenotransplantation. Such tissues lack the α(1,3) galactosyl (gal) epitopes that are responsible for hyperacute rejection in primates and comprise GGTA1 null cells. Such tissues are derived from a swine according to the first or the second aspect of the invention. For purposes of the invention, a "tissue" is an organized structure comprising cells, which tissue, alone or in conjunction with other cells or tissues, performs one or more biological function.

In a seventh aspect, the invention provides a method for making viable GGTA1 null swine. The method according to this aspect of the invention comprises selecting GGTA1 null cells, enucleating an oocyte, fusing the oocyte with the GGTA1 null cell to yield an NT-derived embryo, and implanting the NT-derived embryo into a surrogate mother, wherein the surrogate mother has initiated estrus, but has not yet completed ovulation.

In certain preferred embodiments, the GGTA1 null cells come from a clonal population of GGTA1 null cells.

In certain preferred embodiments, the oocyte is obtained from a gilt. In certain preferred embodiments, the oocyte is obtained from a sow. In certain preferred embodiments, the donor cell is a primary fibroblast.

In certain preferred embodiments the donor cell is fused with the enucleated oocyte. Alternatively, the nucleus of the donor cell can be directly injected into the cytoplasm of the enucleated oocyte.

In certain preferred embodiments, the NT-derived embryo is implanted in the uterus of the surrogate mother together with parthenogenetic embryos. Parthenogenetic embryos as used herein mean non-viable embryos i.e. embryos without the ability to further divide and survive through to term. In certain preferred embodiments, the NT-derived embryo is implanted in the uterus of the surrogate mother after the surrogate mother has been bred. In some, but not all preferred embodiments, the oocytes are in vitro matured. In some preferred embodiments, the surrogate mother is a gilt. In some preferred embodiments, the surrogate mother is a sow.

In certain preferred embodiments, the oocyte has been enucleated. In certain preferred embodiments, the nucleus of the donor cell is injected into the cytoplasm of the enucleated oocyte.

In certain preferred embodiments, the donor cell is a porcine fetal fibroblast. In certain preferred embodiments, the NT-derived embryo is implanted in the uterus of the non-bred surrogate mother. In some, but not all preferred embodiments, the oocytes are in vitro matured.

In certain preferred embodiments, the donor cell is derived from a porcine fetal fibroblast cell heterozygous for a GGTA1 knockout.

In some preferred embodiments, the surrogate mother is a gilt. In some preferred embodiments, the surrogate mother is a sow.

In an eighth aspect, the invention provides a method of creating a viable GGTA1 null swine comprising enucleating an oocyte, fusing the oocyte with a cell derived from Q2 to yield an NT-derived embryo, and implanting the NT-derived embryo into a surrogate mother, wherein the surrogate mother has initiated estrus, but has not yet completed ovulation. All other parameters are as described for the eighth aspect.

In a ninth aspect, the invention provides a method of creating a viable GGTA1 null knockout swine comprising enucleating an oocyte, fusing the oocyte with a cell derived from Q9 to yield an NT-derived embryo, and implanting the NT-derived embryo into a surrogate mother, wherein the surrogate mother has initiated estrus, but has not yet completed ovulation. All other parameters are as described for the eighth aspect.

In a tenth aspect, the invention provides a method of creating a viable GGTA1 null swine comprising enucleating an oocyte, fusing the oocyte with a cell derived from Q32 to yield an NT-derived embryo, and implanting the NT-derived embryo into a surrogate mother, wherein the surrogate mother has initiated estrus, but has not yet completed ovulation. All other parameters are as described for the eighth aspect.

In an eleventh aspect, the invention provides a method of creating a viable GGTA1 null swine comprising enucleating an oocyte, fusing the oocyte with a cell derived from Q37 to yield an NT-derived embryo, and implanting the NT-derived embryo into a surrogate mother, wherein the surrogate mother has initiated estrus, but has not yet completed ovulation. All other parameters are as described for the eighth aspect.

Certain advantageous features of the invention will become evident from the following examples. Cells lacking expression of GGTA1 are useful for the study of cellular processes in the absence of the enzyme, assay of serum reactivity in the absence of $\alpha$-1,3-gal epitopes and the generation of GGTA1 null animals. The latter use requires isolation of cells with a stable genetic modification that prevents expression of the enzyme.

Previous efforts to isolate GGTA1 null cells beginning with GGTA1 heterozygous cells have utilized transfection with a gene targeting vector combined with a drug selection system that differs from that used to select the heterozygous cells. See Gustaffson et al U.S. Pat. No. 6,153,428. Development and application of a second drug selection system has not been successful to date.

In contrast, the present invention involves selection of cells with mutations in the functional allele of heterozygous GGTA1 cells or somatic recombination leading to GGTA1 null cells without using a second drug selector such as G418. Repeated selection against cells expressing GGTA1 is performed by exposure to affinity purified primate antibodies against the $\alpha$-1,3-gal epitope followed by lysis with complement. As an alternative or supplement treatment, depletion of cells expressing GGTA1 is performed by, with or without first treating the cells with anti-gal reagents, including but not limited to, gal epitope ligands or anti-galactose-$\alpha$(1,3)-galactose antibodies, followed by using the appropriately coated magnetic micro-beads. The antibody/complement treatment and the depletion can be repeated multiple times in any order. Use of the above processes results in a population of cells sufficiently enriched in GGTA1 null cells for direct use in nuclear transfer. Alternatively, enriched cell populations may be cloned, with or without additional selection with antibody and complement or depletion as described above. Similar selection may be performed with other agents which specifically bind the $\alpha$-1,3-gal epitope and lead to cell death or permit physical separation of binding and non-binding cell populations.

The invention, in conjunction with nuclear transfer, allows for the production of animals containing mutant alleles of the GGTA1 locus that lack foreign DNA sequences. Animals homozygous for such alleles would be preferred for use in clinical xenotransplantation. Alternatively, such alleles would permit additional genetic modifications to be introduced using the same selection system as originally utilized for the isolation of GGTA1 heterozygous cells.

The following examples are intended to further illustrate certain particularly preferred embodiments of the invention and are not intended to limit the scope of the invention in any way. Except as otherwise noted, all chemicals are from Sigma (St. Louis, Mo.).

EXAMPLE 1

Selection and Analysis of Cell Populations Lacking $\alpha$-1,3-gal Epitope Expression The ability to select populations of cells lacking $\alpha$-1,3-gal epitope expression was tested by multiple selection of GGTA1 heterozygous 355-F3 cells with anti-$\alpha$-1,3-gal antibody and complement. GGTA1 heterozygous cells were isolated from a nuclear transfer fetus (355-F3) at day 32 of gestation and cultured as described (Lai et al., Science 295: 1089). The donor cells for reconstruction of nuclear transfer embryos leading to the fetuses were explanted and cultured from ear sections of pig O212-2, a GGTA1 heterozygote in which one allele has been inactivated by homologous recombination with vector pGalGTΔS-Neo (Lai et al., Science 295: 1089, 2002). 355-F3 cells were cultured in F10 medium containing 20% FBS and 20 ug/ml gentamycin (media) on collagen I coated dishes at 5% $CO_2$, 3% $O_2$, and 37° C. Antibodies against $\alpha$-1,3-gal epitope were purified from naïve baboon plasma and was adsorbed on $\alpha$Gal sugar using the $\alpha$-1,3-gal LB-VI matrix column (Alberta Research Council, Canada.) The bound antibody was eluted from the column by low pH (0.25% acetic acid, Abbot Labs,) into a TRIS based salt buffer (0.2M TRIS and 0.6M Sodium Chloride.) Eluted fractions were dialyzed against PBS to equilibrate the buffer to PBS. The antibody batch was concentrated in Amicon Centripreps with a cut-off weight of 30K and then in Centriplus Concentrators with a 50K cut-off weight. The concentrated antibody was dialyzed against PBS, and the concentration determined by UV absorbance and Bradford protein assay. Final stock solutions were diluted to 5 mg/mL and frozen at −80° C.

The above cell lines were treated in suspension at $2-3\times10^6$ cells/ml in 50-100 µg/ml of affinity purified anti-α1,3-gal antibody (Nab) in media for 30 minutes at room temperature with mixing. After washing, cells were then treated with rabbit complement (1:8) (C') containing DNase I (10 µg/ml) in media for 45 min at room temperature with mixing. Surviving cells were counted and plated in bulk culture, and expanded for subsequent treatments. A total of six Nab/C' treatments were done, with treatment numbers 1-3 at 50 µg/ml anti-α1,3-gal antibody and 4-6 at 100 ug/ml. Treatments were performed every 7-9 days. Prior to each antibody/complement treatment, cells were analyzed for the presence of α-1,3-gal epitopes with IB4-FITC. FIG. 1 shows that initial populations of 355-F3 and PFF-F12 (wild-type fetal fibroblasts) cells stain brightly with the α-1,3-gal epitope specific lectin IB4. Selection with antibody and complement resulted in 355-F3 derived populations with very little if any specific IB4 staining after 4 treatments. In contrast, selected wild-type cells showed a much lower decrease in mean IB4 staining. In both cases, multiple selections with antibody and complement resulted in populations highly enriched for cells resistant to lysis by additional antibody/complement treatment. Analysis of 355-F3 derived cells 22 days following the last ($6^{th}$) treatment showed no increase in mean IB4 binding. Similar analysis of PFF-F12 cells 17 days following the last treatment showed a slight increase in mean IB4 binding.

EXAMPLE 2

Selection and Analysis of Cell Clones Lacking Wild-type GGTA1 Expression

Figure 2:
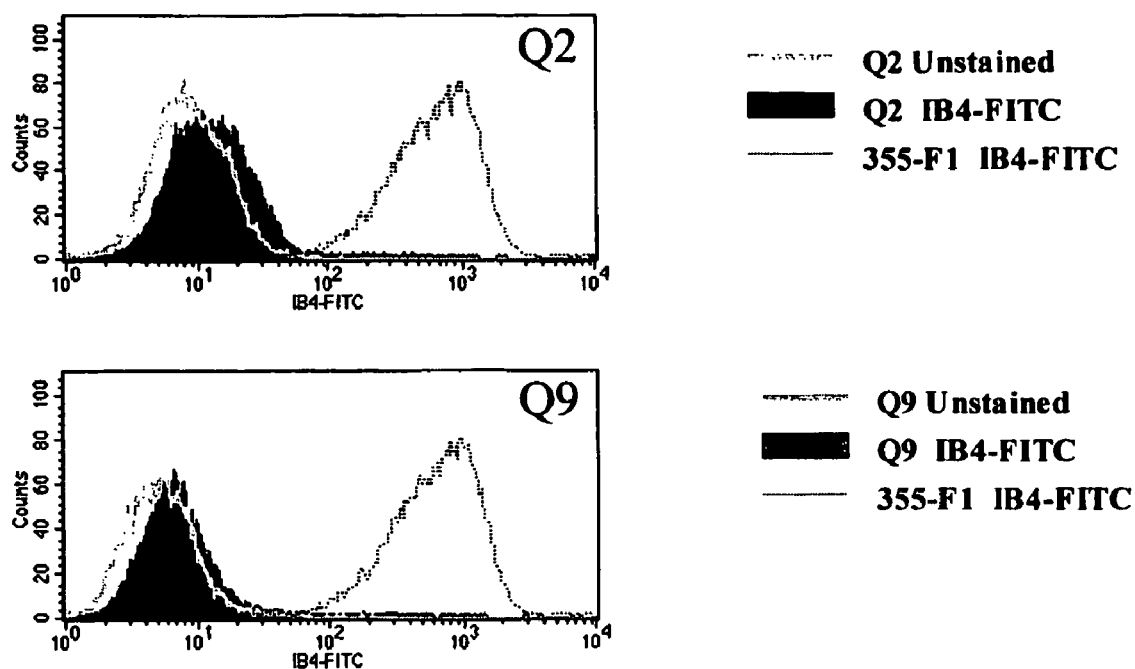
FIG. 2. Flow cytometric analysis of clones Q2 and Q9, derived by antibody/complement selection of GGTA1 heterozygous cells from fetus 355-F1. Selected clones were analyzed prior to and following staining with α(1,3)-gal epitope specific lectin IB4 and compared with staining of the parental fetal cell lines without antibody/complement selection. Very low level staining of the selected clones is seen, possibly due to background binding to non-gal epitopes.

GGTA1 heterozygous 355-F1 cells were isolated from a nuclear transfer fetus (355-F1) at day 32 of gestation and cultured as described (Lai et al., Science 295:1089. The donor cells for reconstruction of nuclear transfer embryos leading to the fetuses were explanted and cultured from ear sections of pig O212-2, a GGTA1 heterozygote in which one allele has been inactivated by homologous recombination with vector pGalGTΔS-Neo (Lai et al., Science 295:1089, 2002). Cells were cultured in F10 medium containing 20% FBS and 20 µg/ml gentamycin (media) on collagen I coated dishes at 5% $CO_2$, 3% $O_2$, and 37° C. The cells were then treated with antibody and complement twice in suspension as above prior to plating at low density for isolation of clones lacking α(1, 3)-gal epitope expression. After the second treatment, cells were plated at 5 and 10 cells/well in collagen I coated 96 well plates. In situ treatments with 100-500 µg/ml anti-α(1,3)-gal antibody for 1 hr 37° C. and 1:8 rabbit complement in for 1 hr 37° C. were performed every other day for treatments 3-5. Wells containing patches of cells covering greater than 15% of the well were transferred to a 48 well plate and treated the following day in situ with 500 µg/ml anti-α1,3-gal antibody and complement. Cells were passaged for molecular analysis, IB4-FITC analysis, and freezing. RNA and ethanol precipitated DNA were prepared using RNeasy and DNeasy systems from Qiagen. Wells containing viable cells following the last treatment were cultured without further selection and lysis resistant clones analyzed for epitope and RNA expression, as well as GGTA1 locus structure. Analysis of two representative clones, Q2 and Q9, is shown in FIGS. 2 and 3. Both clones had little or no specific IB4 binding (FIG. 2). Approximately 50 ng of Q2 and Q9 RNA was reversed transcribed into cDNA using AMV Reverse Transcriptase XL (Takara Shuzo Co., Ltd.) cDNA was then amplified in reactions using LA Taq DNA polymerase (Takara Shuzo Co., Ltd.), the GGTA1 exon 2 forward primer GT-598 (5'-TTCTGCAGAGCAGAGCT-CAC; SEQ ID NO: 1) and the exon 9 reverse primer RN1 (5'-CCCTCAACCCAGAACAGATAAG; SEQ ID NO: 2). PCR products were analyzed on a 1% gel. Southern blots of the RT-PCR products were hybridized to oligonucleotide R823 (5'-AGGATGTGCCTTGTACCACC; SEQ ID NO: 3), which detects transcripts derived from both gene targeted and native GGTA1 loci. A 1421 base pair band is expected for the native locus and 2472 base pair band for the targeted locus. RT-PCR analysis of the clones (FIG. 3) resulted in a band compatible with expression from the gene targeted locus present in Q2 and Q9 cells, but no band compatible with expression from a wild-type GGTA1 locus. Approximately 200 ng of DNA was amplified, cut and analyzed on agarose gels as described (Lai et al., Science 295:1089), except that the 5' genomic assay utilized primers F248 (5'-GAAGAA-GACGCTATAGGCAACG; SEQ ID NO: 4) and RN1 in place of F238 and R823. To increase sensitivity of detection, DNA from the gels was transferred to nylon membranes and hybridized to oligonucleotide probe R823 as above. Hybridizing Eco RI bands of approximately 2550 bp and 3600 bp are expected in the 5' genomic assay from native and targeted GGTA1 loci respectively. Hybridizing Sac I bands of approximately 1250 bp and 2300 bp are expected in the 3' genomic assay from native and targeted GGTA1 loci respectively. Genomic PCR analysis (FIG. 3), revealed the presence of a GGTA1 locus with a structure expected from the gene targeted locus in 355-F1 cells, but no locus with a structure like that of the wild-type GGTA1 locus.

EXAMPLE 3

Production of Piglets Using Cell Clones Lacking Wild-type GGTA1 Expression

Figure 4:
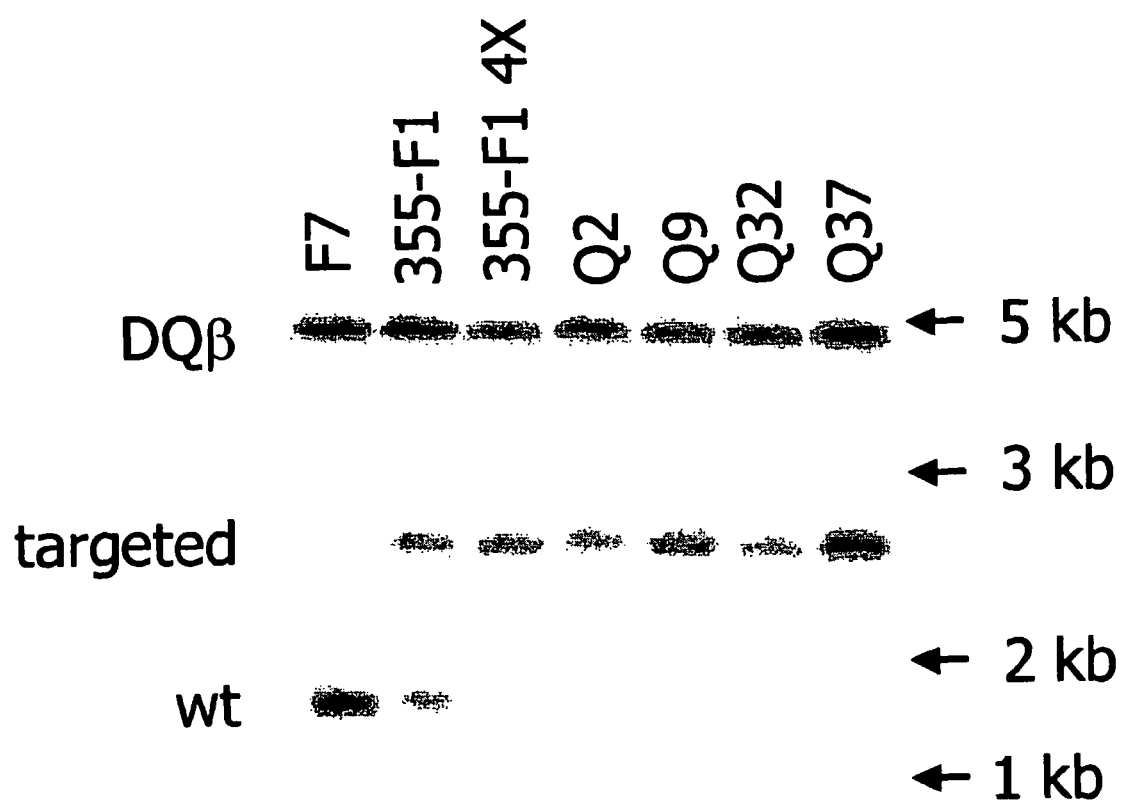
FIG. 4. Quantitative southern blot analysis of nuclear transfer donor lines. Genomic DNA from the indicated sources was digested with restriction enzyme Afl III and hybridized simultaneously with a 116 bp probe from exon 9 of the GGTA1 locus and a 107 bp probe from the DQβ locus (as an internal quantitation control). The GGTA1 probe hybridizes a 1.3 kb wt fragment and a 2.3 kb gene targeted band containing an IRES-neo selection cassette. The F7 sample was prepared from fibroblasts of a wild-type fetus. The 355-F1 sample was prepared from GGTA1 heterozygous fetal fibroblasts prior to selection with natural antibody and complement. The 355-F1 4× sample was prepared from a cell population selected four times with affinity purified baboon natural antibody and complement. Q series samples were from clonal cell lines selected from 355-F1 fetal fibroblasts. The wild-type GGTA1 allele is not detected in the uncloned 4× selected population or in any of the four Q clones.

Nuclear transfer was performed using clonal cell lines Q2 and Q9 (described above) and lines Q32 and Q37, produced at the same time using the same methodology. FIG. 4 shows a genomic southern blot of DNA from the four clones hybridized to a probe from the GGTA1 gene, confirming the absence of a wild-type GGTA1 allele in all of the cloned cell lines. Embryos reconstructed by nuclear transfer using the Q32 cell line were transferred to 6 surrogate gilts, 3 of which established pregnancies as determined by ultrasound examination. One of these pregnancies continued to term and delivered two piglets following caesarian section (piglets O177-1 and O177-2).

Figure 5:
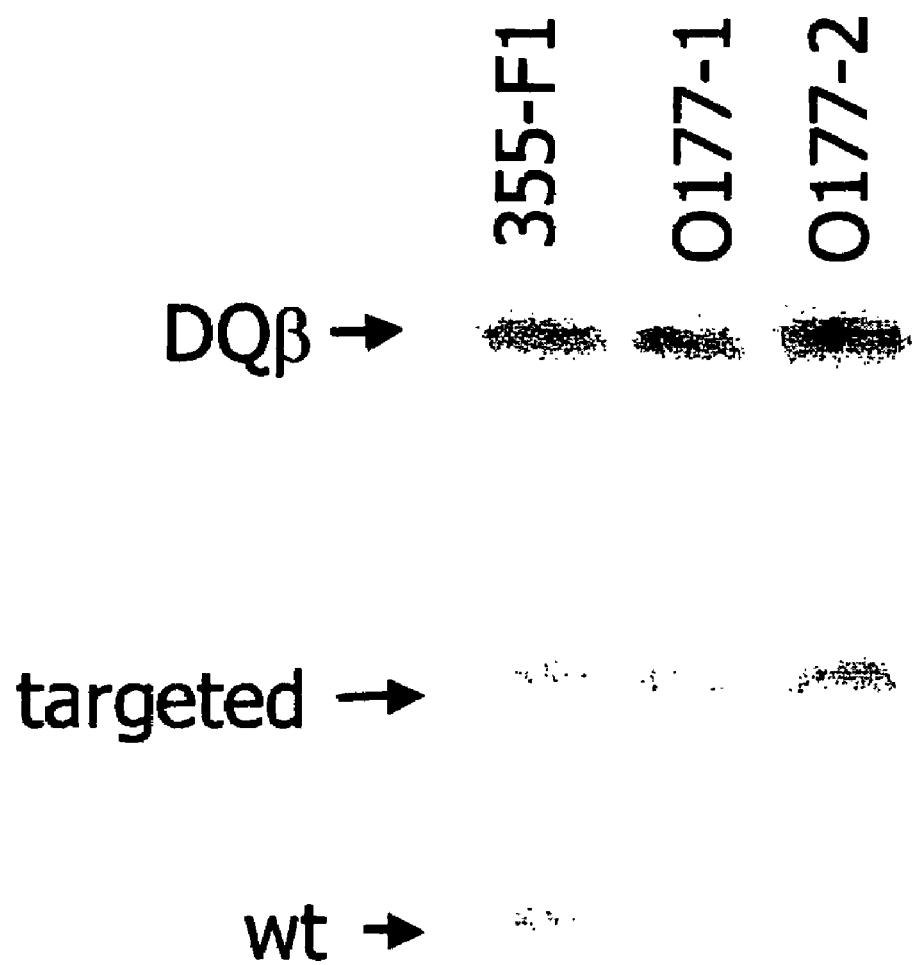
FIG. 5. Southern blot analysis of GGTA1 null piglets. Analysis was performed as described in the legend to FIG. 4. Neither piglets O177-1 nor piglet O177-2 contains a wild-type allele of the GGTA1 gene.
Figure 6:
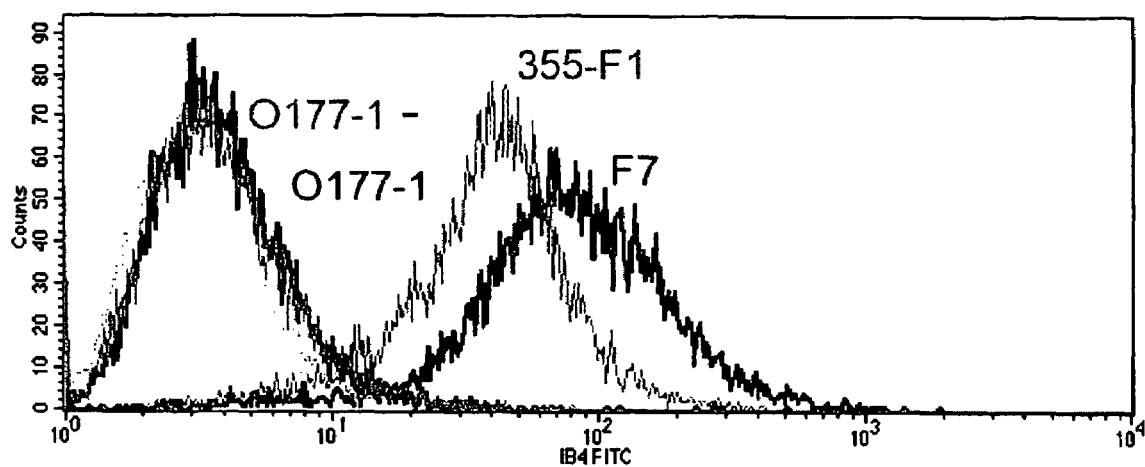
FIG. 6. Flow cytometry analysis of α(1,3)-gal epitopes on GGTA1 null piglet O177-1. Unfixed, cultured fibroblasts from piglet O177-1, heterozygous fetus 355-F1 and wild-type fetus F7 were stained with FITC conjugated IB4 prior to flow analysis. Normal human dermal fibroblasts (NHDF) and unstained O177-1 fibroblasts (−) were used as a negative controls.
Figure 7:
FIG. 7. Piglet O177-1 at two months of age.

Genomic southern blot analysis of DNA prepared from ear fibroblasts confirmed the absence of a wild-type GGTA1 allele in both piglets (FIG. 5). Expression of α-1,3-gal epitopes in ear fibroblasts of piglet O177-1 was examined by flow cytometric analysis following staining with IB4-FITC and was negative, confirming the absence of α-1,3-galactosyltransferase activity in this GGTA1 null animal (FIG. 6). A photograph of piglet O177-1 at 2 months of age is included as FIG. 7.

EXAMPLE 4

Selection and Analysis of Cell Clones Lacking Wild Type GGTA1 Expression Following Depletion Using Magnetic Micro-beads 15541 fibroblasts were obtained from ear punches of GGTA1 heterozygous piglet 15541 by enzymatic digestion as previously described. $2\times10^7$ cells, at a concentration of $2\times10^6$ cells/ml, were stained for 10 minutes at 37° C. with 2 µg/ml of IB4-Biotin (SIGMA, L2140) in IB4 Isolation Buffer (1×PBS containing magnesium and calcium, 0.5% dialyzed BSA). The cells were then washed twice with the isolation buffer and centrifuged for 5 minutes at 200×g. The cells were adjusted to $1.25\times10^8$ cells/ml in isolation buffer and anti-biotin micro beads (Miltenyi Biotec, 130-090-485) were added at 20 µl per $10^7$ cells. The bead and cell mixture was incubated for 30 minutes at 4° C., with agitation every 10 minutes. Cells were washed with the isolation buffer and centrifuged for 5 minutes at 200×g. Cells were then suspended in 0.5 ml of isolation buffer and passed through a 40 micron straining filter. The filter was rinsed with an additional 0.5 ml of isolation buffer and the cells applied to a MACS LD (Miltenyi Biotec, 130-042-901) depletion column with the appropriate magnet. The flow through was collected as the putative gal eptiope negative cell population and subcloned at ⅓ cell per well into collagen I coated 96 well microtiter plates. Cell clones were isolated 11-14 days later and expanded for analysis and cryopreservation.

Figure 8:
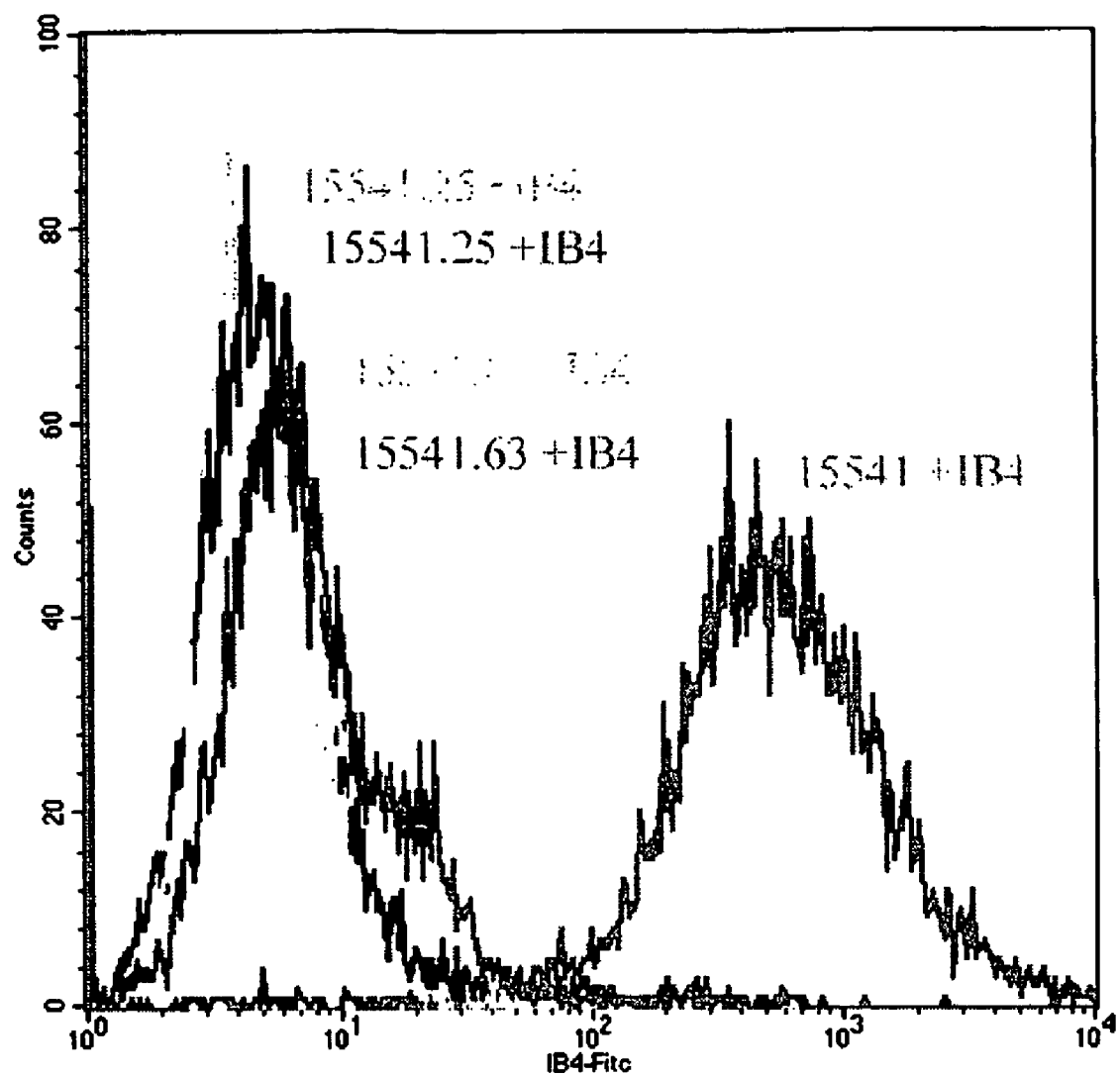
FIG. 8. Flow cytometry analysis of α(1,3)-gal epitopes on cell clones derived from heterozygous cells following depletion with IB4-FITC and anti-FITC magnetic beads. Analysis of clones 15541.25 and 15541.63 is shown with (+) and without (−) IB4-FITC staining.

Clones 15541.25 and 15541.63 were examined for expression of gal epitopes by flow cytometric analysis following staining with FITC conjugated IB4 lectin (FIG. 8). Fluorescence for both clones was indistinguishable from that seen without IB4-FITC staining.

Figure 9:
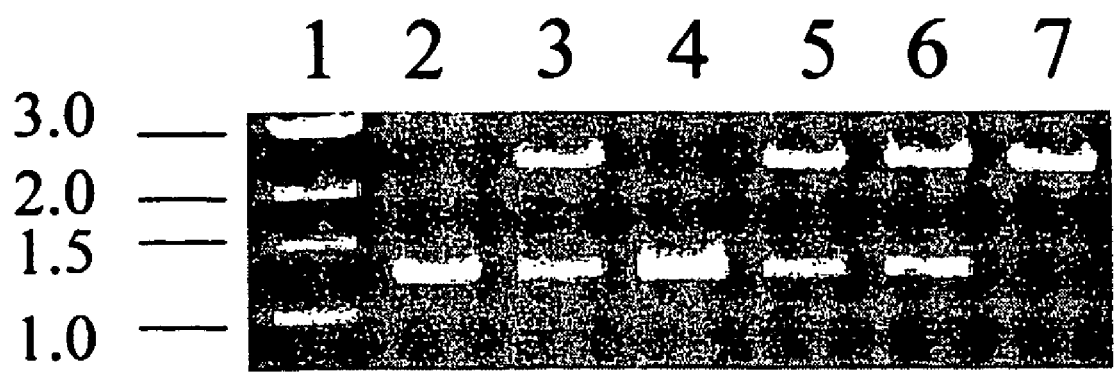
FIG. 9. Genomic analysis of clones 15541.25 and 15541.63, derived by IB4-FITC/magnetic bead depletion of GGTA1 heterozygous cells from piglet 15541. 3' targeting analysis was performed as described for FIG. 3B. Lane 1: Molecular weight markers, sizes are indicated in kbp. Lane 2: Wild-type fetus F3. Lane 3: Heterozygous sow O226-1, mother of piglet 15541. Lane 4: Wild-type boar 14925, father of piglet 15541. Lane 5: Heterozygous piglet 15541. Lane 6: Clonal cell line 15541.25, cloned from 15541 cells following magnetic bead depletion of 15541 cells. Lane 7: Clonal cell line 15541.63, cloned from 15541 cells following magnetic bead depletion of 15541 cells. A 2.3 kbp targeted locus and 1.25 kbp wild-type locus PCR products are detected in 15541 cells prior to selection, but only the 2472 bp product is detected in clone 15541.63. Clone 15541.25 yields products consistent with one targeted allele and one allele similar in size to a wild-type allele.

DNA was prepared from clones 15541.25 and 15541.63 and analyzed by 3' genomic PCR analysis as described for FIG. 3B (FIG. 9). Clone 15541.25 was found to contain a single gene targeted allele and a second allele similar in size to a wild-type allele; the exact nature of the GGTA1 mutation in this clone has not been determined. Clone 15541.63 was found to lack a wild-type GGTA1 allele, as seen previously with GGTA1 null cell clones Q2, Q9, Q32 and Q37.

EXAMPLE 5

Figure 10:
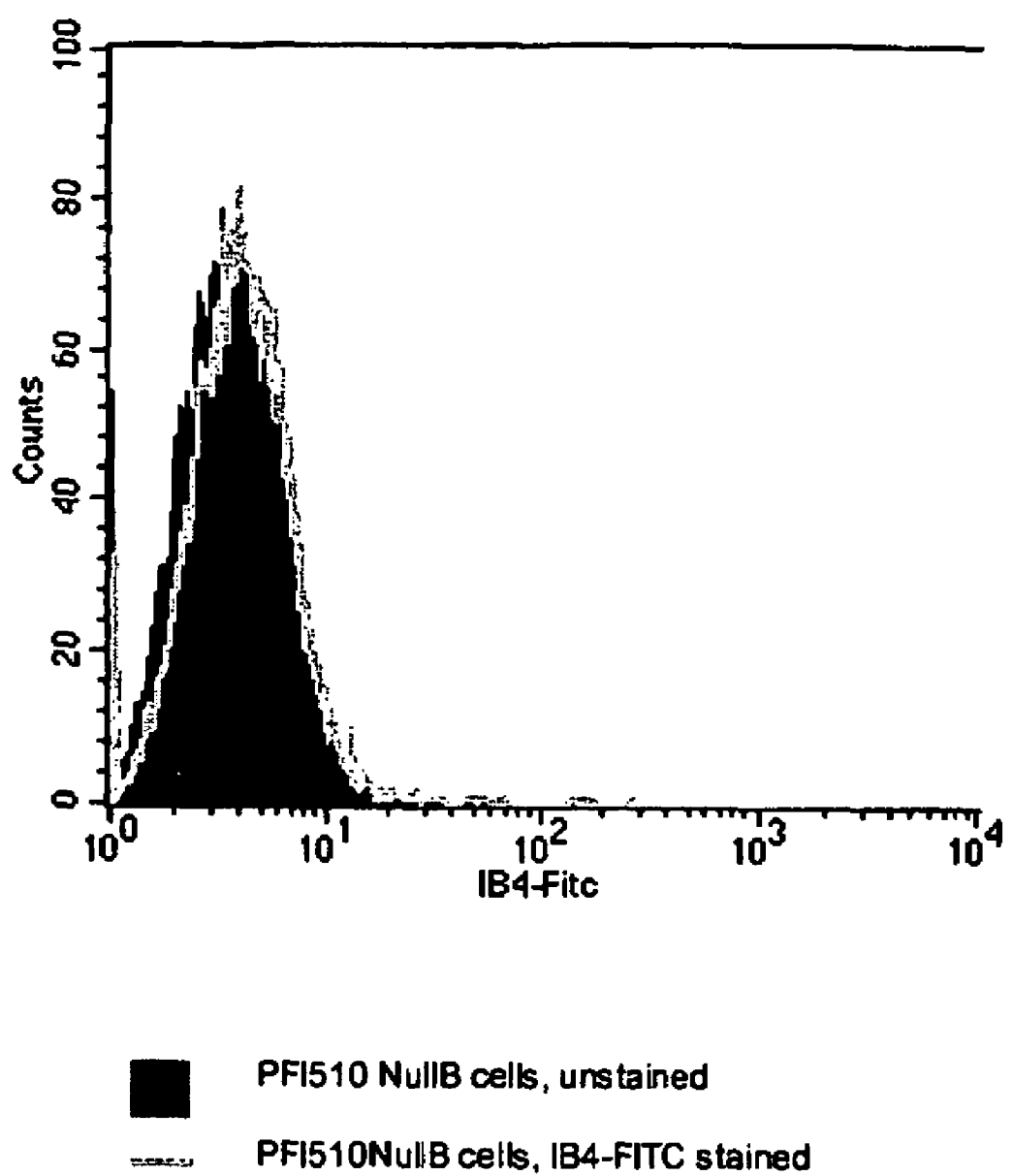
FIG. 10. Flow cytometry analysis of PFI510 NullB cells, with and without IB4-FITC staining.

Production of Piglets Using Uncloned Cell Populations Depleted of Gal Epitope Bearing Cells Cells from GGTA1 heterozygous fetus PFI510 were subjected to 3 rounds of antibody/complement lysis as described in Example 1, followed by 3 rounds of depletion using IB4-FITC and anti-FITC magnetic micro-beads as described in Example 4. IB4-FITC staining of the depleted cell population (PFI510 NullB cells) is shown in FIG. 10.

Figure 11:
FIG. 11. Piglet PL751 at 4 days of age.
Figure 12:
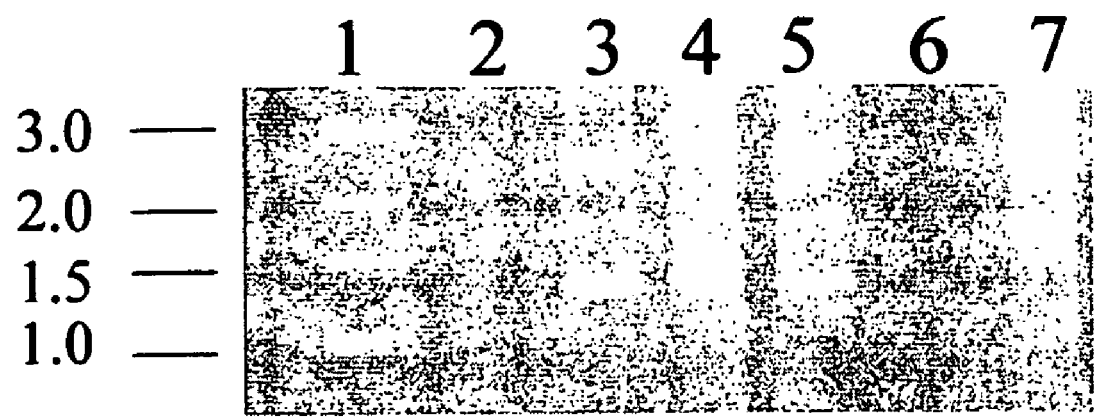
FIG. 12. Genomic analysis of piglet PL751 3' targeting analysis was performed as described for FIG. 3B. Lane 1: Molecular weight markers, sizes are indicated in kbp. Lane 2: No DNA. Lane 3: Heterozygous fetus PF15 10. Lane 4: Wild-type fetus F505. Lane 5: GGTA1 heterozygous control cell line PED D.13. Lane 6: No DNA. Lane 7: Piglet PL751. Only the 2472 bp product derived from a gene targeted allele is detected in the piglet.
Figure 13:
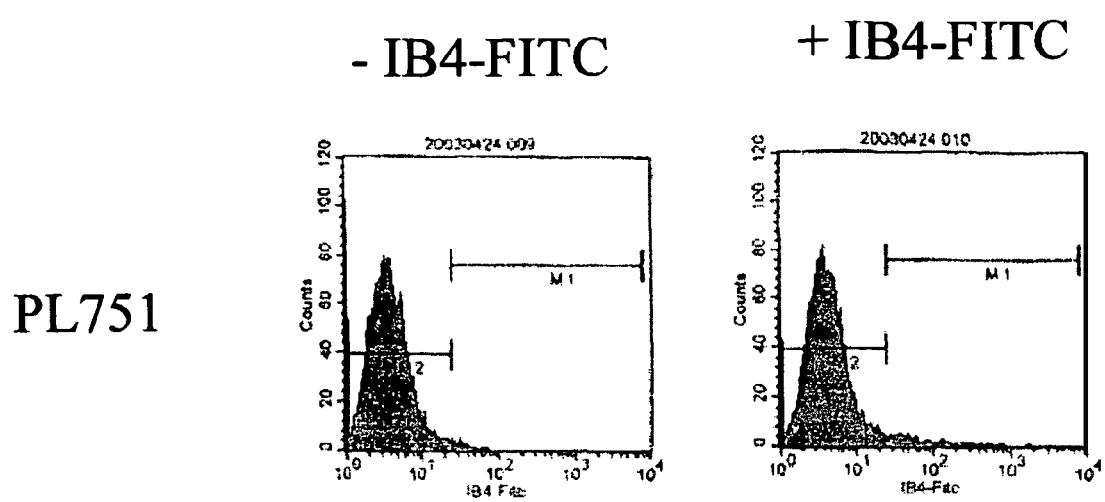
FIG. 13. Flow cytometry analysis of ear fibroblasts from piglet PL751, with and without IB4-FITC staining.

Nuclear transfer was performed using PFI510 NullB cells as the donor line. Embryo recipient 1538 delivered one surviving piglet, PL751 (FIG. 11). Analysis of genomic DNA from this piglet confirmed the absence of a WT GGTA1 allele, as seen previously with piglets derived from clonal cell lines selected with natural antibody and complement (FIG. 12). Flow analysis of ear fibroblasts from PL751 also revealed the absence of IB4 lectin staining cells (FIG. 13).

What is claimed is:

1. A method of selecting GGTA1 null cells comprising the steps of:
   (a) obtaining a line of cells obtained from a GGTA1 heterozygous swine or swine fetus;
   (b) enriching the cells for GGTA1 null cells by treating the cells with agents that specifically bind an α(1,3)-galactose epitope and that deplete cells that express the epitope; and
   (c) scanning the line for viable GGTA1 null cells.

2. The method of claim 1 wherein in step (b), the cells are enriched by at least one treatment selected from the group consisting of: (a) treating the said cells with anti-galactose-α(1,3)-galactose antibodies, in the presence of complement; (b) depleting the said cells with magnetic micro-beads bound with anti-gal reagents; (c) treating the said cells with anti-galactose-α(1,3)-galactose antibodies and depleting the said cells with magnetic micro-beads bound with anti-antibodies; and (d) treating the said line with gal epitope ligands and depleting the said line with magnetic micro-beads bound with anti ligand antibodies.

3. The method of claim 1 wherein in step (b), the cells are enriched by multiple treatments selected from the group consisting of: (a) treating the said cells with anti-galactose-α(1,3)-galactose antibodies, in the presence of complement; (b) depleting the said cells with magnetic micro-beads bound with anti-gal reagents; (c) treating the said cells with anti-galactose-α(1,3)-galactose antibodies and depleting the said cells with magnetic micro-beads bound with anti-antibodies; and (d) treating the said cells with gal epitope ligands and depleting the said line with magnetic micro-beads bound with anti ligand antibodies.

4. The method of claim 1 wherein in step (b), the cells are enriched by three treatments of each of the following: (a) treating the said cells with anti-galactose-α(1,3)-galactose antibodies, in the presence of complement; (b) treating the said cells with gal epitope ligands and depleting the said line with magnetic micro-beads bound with anti ligand antibodies.

5. The method according to any of claims 1-4 wherein the line of cells is a line of swine fetal fibroblast cells.

6. The method according to any of claims 1-4 wherein the line of cells is a clonal population of swine fetal fibroblast cells.

7. The method of claim 5 wherein the swine fetal fibroblast cells originate from miniature swine.

8. The method according to claim any of claims 1-4 wherein the line of cells is a line of stem cells.

9. The method of claim 8 wherein the stem cells are primordial stem cells.

10. The method according to any of claims 2-4 wherein the anti-galactose-α(1,3)-galactose antibodies are primate antibodies.

11. The method according to any of claims 2-4 wherein the anti-galactose-α(1,3)-galactose antibodies are monoclonal antibodies or fragments thereof.

12. The method according to any of claims 2-3, wherein the anti-gal reagents are selected from a group consisting of anti-galactose-α(1,3)-galactose antibodies and lectin.

13. The method according to any of claims 2-4, wherein the gal epitope ligands are IB4 conjugates and the anti-epitope ligands are anti-IB4 conjugates.

14. The method according to claim 13 wherein the IB4 conjugates are selected from a group consisting of IB4 biotin and IB4-FITC and the anti-IB4 conjugates are selected from a group consisting of anti-biotin and anti-FITC.

15. The method of claim 6 wherein the swine fetal fibroblast cells originate from miniature swine.

\* \* \* \* \*